United States Patent [19]
Provost

[11] Patent Number: 5,840,515
[45] Date of Patent: Nov. 24, 1998

[54] ERYTHROCYTE LYSIS REAGENT, AND ITS USE IN METHODS FOR ISOLATING AND DIFFERENTIATING LEUCOCYTES

[75] Inventor: René Provost, Chateaugiron, France

[73] Assignee: Hycel Diagnostics, Pouilly en Auxois, France

[21] Appl. No.: 662,628

[22] Filed: Jun. 13, 1996

[30] Foreign Application Priority Data

Jun. 13, 1995 [FR] France .................................. 95 07005

[51] Int. Cl.$^6$ .............................. C12Q 1/04; C12Q 1/02; G01N 1/30; G01N 33/483
[52] U.S. Cl. .................... 435/29; 435/34; 435/2; 435/40.51; 436/63; 436/808
[58] Field of Search ............................. 436/17, 18, 808, 436/63; 435/2, 240.2, 372, 325, 355, 40.51, 34, 29

[56] References Cited

U.S. PATENT DOCUMENTS

| | | | |
|---|---|---|---|
| 4,751,179 | 6/1988 | Ledis et al. | 435/34 |
| 5,102,909 | 4/1992 | Veltri et al. | 514/470 |
| 5,516,695 | 5/1996 | Kim et al. | 436/17 |

FOREIGN PATENT DOCUMENTS

| | | |
|---|---|---|
| 0-582 736 | 2/1994 | European Pat. Off. . |
| 85/05640 | 12/1985 | WIPO . |
| 88/07187 | 9/1988 | WIPO . |
| 94/18828 | 9/1994 | WIPO . |

OTHER PUBLICATIONS

Kliman, HJ et al. J. Biol. Chem. 255(13):6314–6321, Jul. 10, 1980.

Humphries, RK and Miller, RG. Ser. Haemat. vol. V, 2, 1972. pp. 142–162.

Abstract of JP4151541 (Hitachi Keisoku Eng KK), May 25, 1992, Database WPI, Week 9227, Derwent Publications Ltd., London, GB.

*Primary Examiner*—David Saunders
*Assistant Examiner*—F. Pierre VanderVegt
*Attorney, Agent, or Firm*—Jacobson, Price, Holman & Stern, PLLC

[57] ABSTRACT

Method for isolating and differentiating leucocytes in a blood sample, comprising the steps of:
- lysis of the erythrocytes with a solution whose osmolality and pH have been adjusted to maintain leucocyte integrity, and containing saponin,
- determination of the point of lysis, and
- inhibition of the lysis by diluting the sample with a solution having substantially a similar composition but not containing saponin.

7 Claims, 5 Drawing Sheets

5,840,515

ERYTHROCYTE LYSIS REAGENT, AND ITS USE IN METHODS FOR ISOLATING AND DIFFERENTIATING LEUCOCYTES

FIELD OF THE INVENTION

This invention relates to a lysis reagent for erythrocytes.

It also relates to a method for isolating, differentiating and quantifying leucocytes, and their different categories, in a blood sample.

BACKGROUND

The object of haematological analysis is to identify and count several categories of cells in order to establish a diagnosis. The cells to be identified are usually leucocytes divided into three main sub-populations, namely lymphocytes, monocytes and granulocytes. The latter comprise, in particular, eosinophils, neutrophils and basophils.

Such analysis is generally carried out with means which use the Coulter effect. Such means involves the passage of the cells in a conducting liquid through an opening of small diameter to which is applied a constant electric current. The passage of a particle at this point produces a transient variation of conductivity corresponding the volume occupied by the particle as it passes through the opening.

These measurements of variation in impedance are, however, known to be insufficient for cell identification. Cells belonging to different families sometimes have very similar volumes.

This is the reason why in addition to these measurements of impedance variation, other measurements are conventionally made using an optical device such as a laser diode. With this type of device, the cells passing through an opening of small diameter are illuminated by a laser beam and reflect the light. The intensity of the light reflected by a cell is in correlation with the refractive index of this cell. Measurement of the reflected light therefore gives information on the surface condition of the cell.

It is found that by using information on cell volume and surface condition, it is possible to obtain a precise analysis.

Whichever means are used for haematological analysis, blood samples for analysis must be prepared previously.

The leucocyte, or white cell, count cannot be made without previous lysis of the erythrocytes, or red cells, the latter being much greater in number (1 per 1000).

Saponin has been used to carry out erythrocyte lysis but it has many disadvantages. Firstly, the action of this enzyme is closely related to the temperature at which the reaction is carried out. Secondly, the kinetics of its reaction are such that it is extremely difficult to determine the stage at which the erythrocytes are removed and the leucocytes remain unimpaired. These two disadvantages are further heightened by the fact that there is substantial heterogeneity between different batches of saponin.

Therefore, lysis using saponin alone might impair the leucocytes, in particular their nucleus, as there is no control over the enzyme reaction.

As saponin alone cannot be used, other molecules, quaternary ammonium compounds such as the bromides or chlorides of tetradecyltrimethylammonium or the chlorides or bromides of dodecyltrimethylammonium have been used for the lysis of erythrocytes. Nevertheless, these quaternary ammonium compounds only allow a distinction to be made between three sub-populations of leucocytes, namely lymphocytes, monocytes and granulocytes.

With the advent of flow cytometers, using the system of hydrodynamic focalisation, it became necessary to use lysis which preserves the morphology and volume of the leucocytes.

The lysis reagents that were subsequently developed consist of two different reagents:
  a hypotonic lysis agent, that is to say one which gives the medium an osmolality of between 50 and 100 milliosmoles, containing saponin for example, and
  a stabilizing agent, in the form of a saline solution, whose effect is to readjust the pH and osmolality of the blood sample and lysis agent mixture.

The addition of this stabilizing agent allows to stop the continuation of the lysis process by inhibiting the saponin. Such agent provides to the solution an osmolality of approximately 300 milliosmoles.

A fixing agent, such as glutaraldehyde, may then be added to this solution in order to stabilize the leucocytes, as described in U.S. Pat. No. 4,751,179, FR patent 2 654 744 and WO 85/05 640.

This lysis process therefore requires the use of at least two different reagents, and consequently needs more complex equipment, a greater number of reagents and more complex programming of the various operations, in particular addition and mixing times.

This solution has numerous disadvantages owing to the presence of two different reagents, one lysing the erythrocytes and the other inhibiting this lysis.

International patent application WO-94/18,828 (ABBOTT Laboratories) disclosed a method for the lysis of blood samples using two ingredients, firstly a non-quaternary ammonium salt, and secondly an aldehyde with a short aliphatic chain. This application describes the optional use of saponin. Nevertheless, on page 18 thereof, it is specified that saponin may cause substantial impairment of leucocyte structure if it is used alone. At all events, saponin is not the essential element of lysis in this application.

It is recalled that the count of the various leucocyte sub-populations is an important part of diagnosis.

None of the methods for determining the leucocyte sub-populations disclosed in the prior art, provides a reliable solution that is simple to perform and can be automated, to this problem in the area of public health.

It emerges from the state of the art described above, that reagents such as ammonium salts were well known, but that they have the particular disadvantage of only being able to distinguish three sub-populations of leucocytes. Also, saponin could not be used alone as it involves the risk of impairing the leucocytes, that is to say precisely those cells which were to be identified.

The most recent solution described above requires the presence of two reagents and therefore the development of more complex equipment.

SUMMARY OF THE INVENTION

To solve these multiple problems it has now been found that it is possible to use saponin to lyse erythrocytes, while nevertheless maintaining leucocyte integrity, by determining through a simple measurement the stage of the lysis reaction at which the erythrocytes are almost entirely lysed but at which the leucocytes do not undergo any impairment, or only very limited impairment, called the point of lysis, and by inhibiting the reaction of saponin.

A particular reagent which provides efficient lysis of the erythrocytes, does not impair the leucocytes and allows measurement of the point of lysis has also been developed.

The object of the present invention is therefore a method for isolating and differentiating sub-populations of leucocytes in a blood sample, comprising the steps of:

lysis of the erythrocytes with a solution whose osmolality and pH have been adjusted to maintain leucocyte integrity, and containing saponin, determination of the point of lysis, and inhibition of the lysis by diluting the sample at the point of lysis with a solution having substantially a similar composition but not containing saponin.

DETAILS

Figure 1:
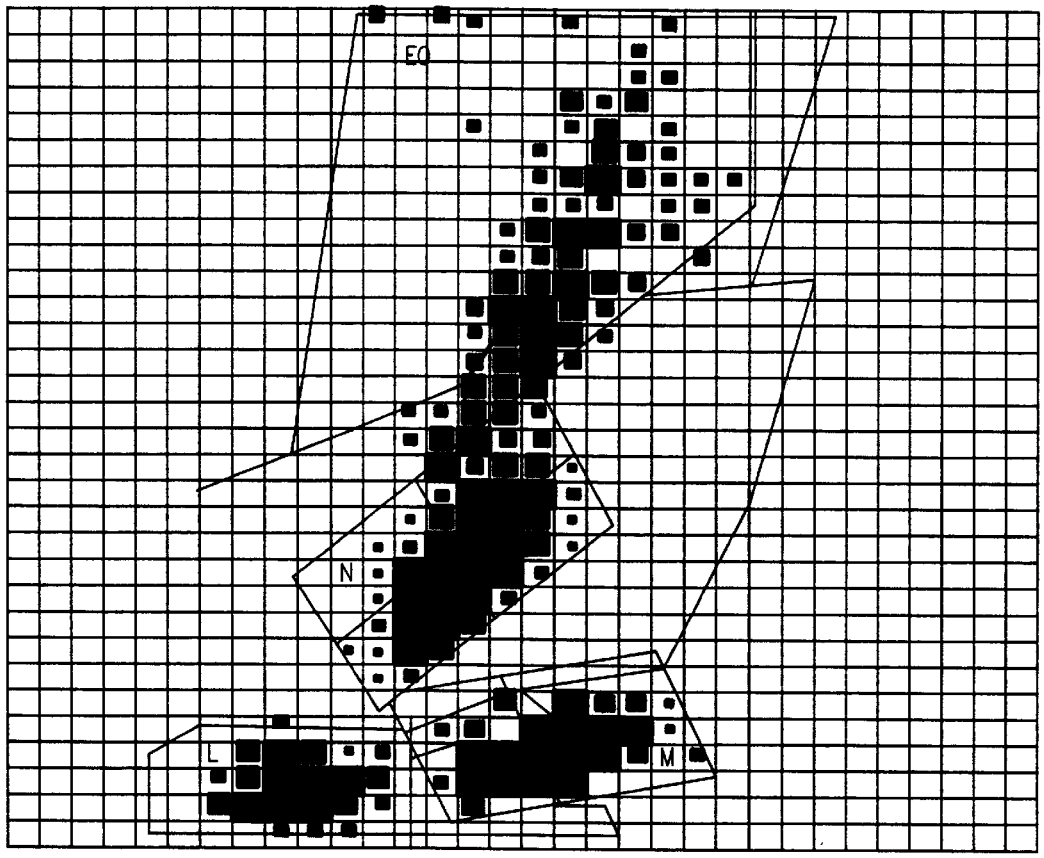
FIGS. 1 to 5 and 7 represent cytograms of blood samples. Distribution is represented along the Y-axis, and cell size on the X-axis.

For the purposes of the present invention, it is considered that the point of lysis is reached when substantially all the erythrocytes have been lysed.

The lysates derived from this isolating method advantageously provide four sub-populations of leucocytes without impairment or a very low impairment and which can be identified by the methods described above. These four sub-populations are:

lymphocytes monocytes neutrophils, and eosinophils.

In particularly advantageous manner, the first step of this method, that is to say lysis of the erythrocytes, is carried out using a reagent comprising from 0.1 to 2g/l, preferably from 0.7 to 1.4 g/l of saponin and whose osmolality lies between 200 and 400 milliosmoles, preferably between 280 and 320 milliosmoles, and whose pH is between 6 and 8, preferably between 6.5 and 7.5.

The saponin used in the present invention may contain 10 to 20% sapogenin, which is the non-glycosylated form of saponin. It may, for example, be that marketed under reference 84510 by the FLUKA company.

Such reagent may also comprise salts and various other molecules intended to maintain the osmolality within the range indicated above and to provide a buffer effect.

The lysis reaction, that is to say the first step of the method described above, is carried out at a temperature at which saponin can cause erythrocyte deterioration, preferably between 15° C. and 45° C. and, further preferably, at approximately 37° C.

The first step of this method is implemented by mixing the sample of human blood with a lysis reagent containing saponin in a volume ratio of between 1:20 and 1:40, preferably near of 1:33.

It is possible to use diluents to dilute the saponin before it is mixed with the blood sample.

Such diluents, also called sheath reagents, may be HEMATON PLUS HYCEL diluent, marketed by HYCEL GROUP LISABID or ISOTON III marketed by the COULTER company.

Inhibition of the reaction may be made using the same diluent or a solution having substantially the same composition.

The volume ratios between the lysate derived from the first two steps of the method and the solution intended to inhibit the action of saponin in the third step, advantageously lie between 2 and 4, preferably in the region of 3.

Determination of the point of lysis may be made using any means but is preferably performed by measurement of the light radiation transmitted through the sample.

Such determination may, in particular, be performed using the method and means disclosed in French Patent Application 95 05 285 filed on May 3, 1995, by the HYCEL GROUP LIPABID: "Method and means of detection of the point of lysis in red cells".

Said method consists of:

mixing the blood sample with saponin, as described above, emitting light rays in the direction of the reaction mixture, receiving the light transmitted through said mixture, and comparing the quantity of light received at a predetermined threshold, the point of lysis being reached when the quantity of light corresponds to said threshold.

The text of the specification (from page 3, line 19, to page 8, line 20)of French patent application 95 05 285 is incorporated in the present application by reference. A certified English translation thereof immediately precedes the claims.

After inhibition of the lysis, that is to say after the third step of the method described above, the lysate is analyzed in a flow cytometer with a laser source by passing the cells through a cytometric chamber allowing differentiation between size (small angles) and granulometry (wide angles).

The method according to the present invention therefore provides numerous advantages in comparison with the methods already described in the prior art:

it provides full control over the lysis reaction of saponin, and therefore enables blood preparations to be obtained which are substantially free of erythrocytes but in which leucocyte integrity has been maintained, it only requires the use of a single type of diluent, in which the lysis reaction is carried out and which is also used to inhibit this reaction, and it allows differentiation between four leucocyte sub-populations, whereas the reagent routinely used can only distinguish between three sub-populations.

The flow cytometers on which the method of the invention can be performed are in particular the HYCEL cytometer, type HEMA 5, marketed by HUYCEL GROUP LISABID, the ATC 3000 manufactured by the Commissariat à l'Energie Atomique, the FASCAN marketed by BECTON-DICKINSON and the EPICS marketed by the COULTER company.

The present invention is illustrated by the following examples.

In these examples, FIGS. 1 to 5 and 7 represent cytograms of blood samples. Distribution is represented along the Y-axis and cell size on the X-axis.

Figure 6:
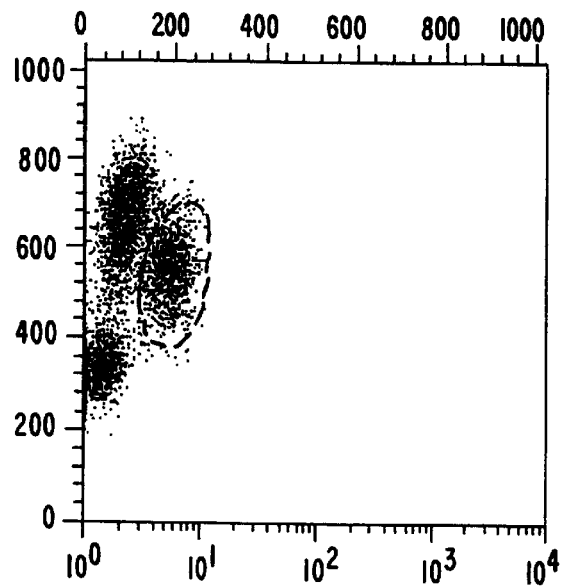
FIG. 6 represents a cytogram in which the fluorescence (X-axis) is measured in relation to distribution(Y-axis).

FIG. 6 represents a cytogram in which the fluorescence (X-axis) is measured in relation to distribution (Y-axis).

EXAMPLE I

Analysis, using a HEMA 5 counter, of a blood sample treated by the method of the invention A blood sample is treated with a lysis reagent comprising a solution of saponin at a concentration of 0.9 g/l in HEMATON PLUS reagent marketed by the HYCEL company.

The lysis reagent is brought to a temperature of 37° C. and then 30 µl of blood sample are mixed with 1 ml of this reagent.

The mixture obtained is shaken.

Complete lysis is obtained after 3 to 20 seconds, according to the samples.

Photometric measurements are carried out to determine the point of lysis.

As soon as it is reached, that is to say as soon as staining of the samples is stable and all erythrocytes have been lysed, the reaction is halted with the addition of 3 ml HEMATON PLUS (sheath reagent) which stops the lysing effect of the saponin.

The samples thus treated are analyzed on HEMA 5 counter.

FIGS. 1 to 4 represent cytograms of four blood samples treated in the manner described above.

On these cytograms four cell populations can be clearly distinguished which correspond to leucocytes, monocytes, neutrophils and eosinophils.

These cytograms show an excellent correlation with analyses of the same blood samples on a COULTER STKS counter.

EXAMPLE 2

Analysis, using an ATC 3000 counter, of blood samples treated by the method of the present invention Blood samples were lysed with a composition comprising 0.3 g/l saponin in HEMATON PLUS HYCEL reagent.

33 μl of blood were added to 5 ml of this lysis reagent.

Lysis was carried out at 20° C. for a maximum period of 140 seconds.

The samples thus treated were analyzed on an ATC 3000 counter.

Figure 5:
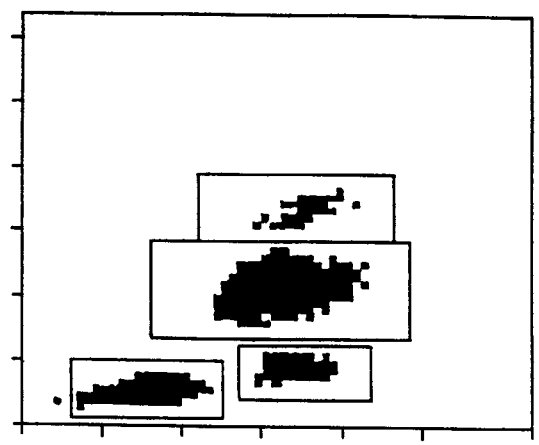

FIG. 5 represents the analysis of a blood sample.

The four sub-populations of leucocytes can be easily distinguished.

The same sample was analyzed on a STKS counter made by the COULTER company.

A good correlation was observed between the analyses made on the two counters.

EXAMPLE 3

Analysis of blood samples, treated according to the Present invention, using a FASCAN cytometer Blood samples were lysed by a lysis reagent containing 3 g/l saponin in HEMATON PLUS HYCEL reagent.

100 μl of human blood were added to 6 ml of this lysis reagent then, after shaking, the sample was analysed on the flow cytometer.

The FASCAN, marketed by the BECTON DICKINSON company, is a flow cytometer with a laser source (excitation at 488 nm) with which fluorescence can be measured.

FIG. 6 represents the fluorescence of blood samples treated in this manner. That part of the figure surrounded by a dotted line represents eosinophils.

Figure 7:
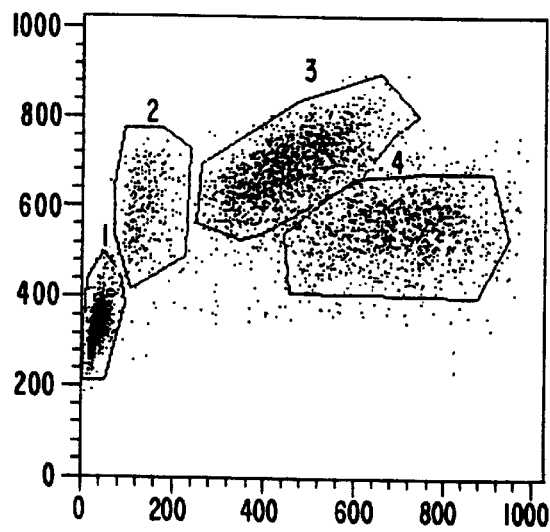

FIG. 7, which illustrates the measurement of cell size, distinguishes between four sub-families of leucocytes numbered 1 to 4 and corresponding respectively to lymphocytes, monocytes, neutrophils and eosinophils.

These results show a good correlation with those obtained with the same blood samples on the SYSMEX NE-8000 apparatus.

Other experiments have shown that the lysis takes very quickly with a high saponin concentration; and raising the temperature accelerates the lysis and allows results to be read off after a very short period.

EXAMPLE 4

Analysis of blood samples, treated by the method of the invention, using an EPICS counter The lysis reagent used in this example consists of a HYCEL reagent in which 0.9 g/l of saponin has been diluted.

100 μl of blood samples were treated with 1 ml of the lysis reagent at 37° C.

The results obtained show a very good correlation with those obtained on other cytometers.

CERTIFIED ENGLISH TRANSLATION

The invention relates to a process consisting of:

preparing a mixture made up of blood and a lysing agent, emitting luminous radiation in the direction of said mixture, receiving the light emitted through said mixture, and comparing the quantity of light received at a predetermined threshold, the point of lysis being reached when the quantity of light corresponds to said threshold.

This process makes it possible to determine the point of lysis for any type of blood and thus to take into account the differences which may exist from one blood type to another.

In a preferred embodiment, the process comprises a further step in which the action of the lysis agent is halted, as soon as the lysis point is reached.

The invention also relates to an apparatus for determining the lysis point of red cells comprising:

an optical apparatus emitting luminous radiation in the direction of a mixture constituted of blood and a lysing agent, means for receiving the light emitted through said mixture, and comparator means, of which a first input corresponds to a threshold value, a second input receiving a signal representative of the light received by said means of reception, the output value of said comparator means being approximately equal to 0 when lysis point is reached.

The following characteristics of the apparatus may also be considered, separately or according to all their possible technical combinations:

the optical apparatus comprises an electro-luminescent diode whose luminous radiation is focused by appropriate means, the means for receiving the light emitted through the mixture are constituted by a photodiode, the photodiode is connected to means delivering a voltage signal representative of the light received by the photodiode, the apparatus includes a tank for the mixture, the apparatus includes means for homogenizing the mixture in the tank, the apparatus includes means for injecting a lysing neutralisation agent.

A clearer picture of the invention, together with other aims, advantages and characteristics will emerge from the ensuing description of non limitative examples of embodiments, which description is to be read in conjunction with the accompanying drawings in which:

FIG. 1 represents schematically an apparatus according to the invention and

Figure 2:
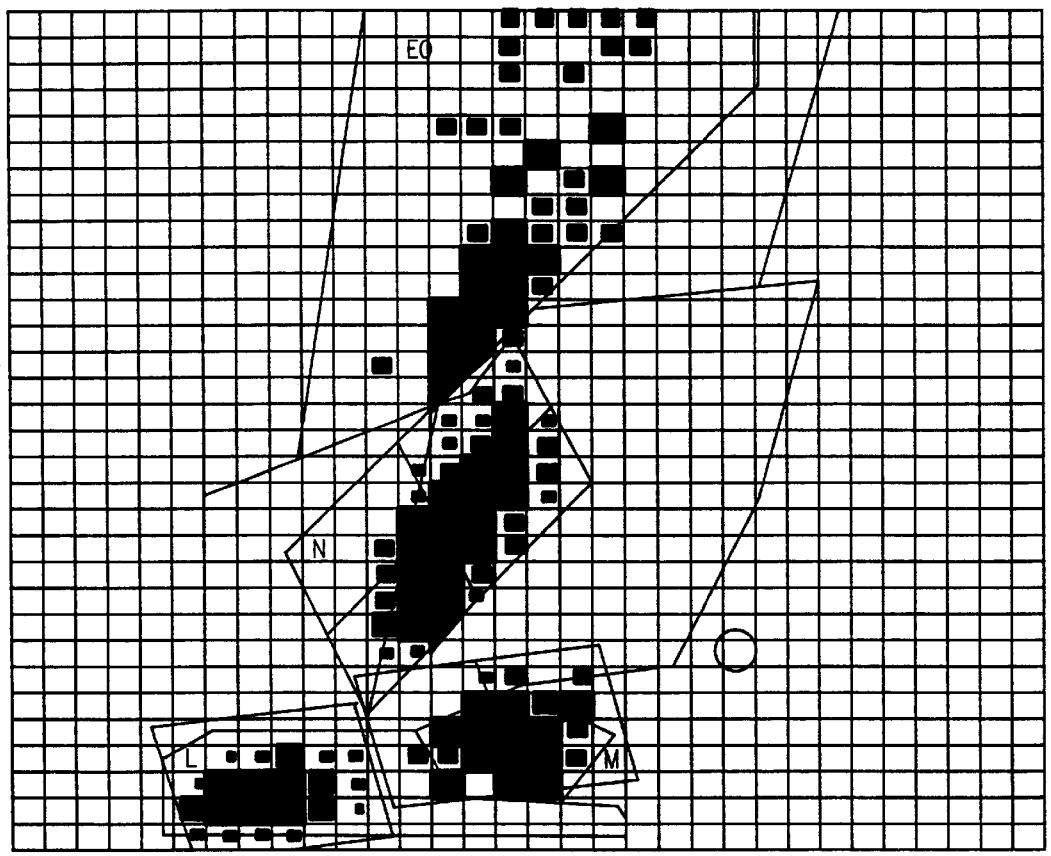
Figure 3:
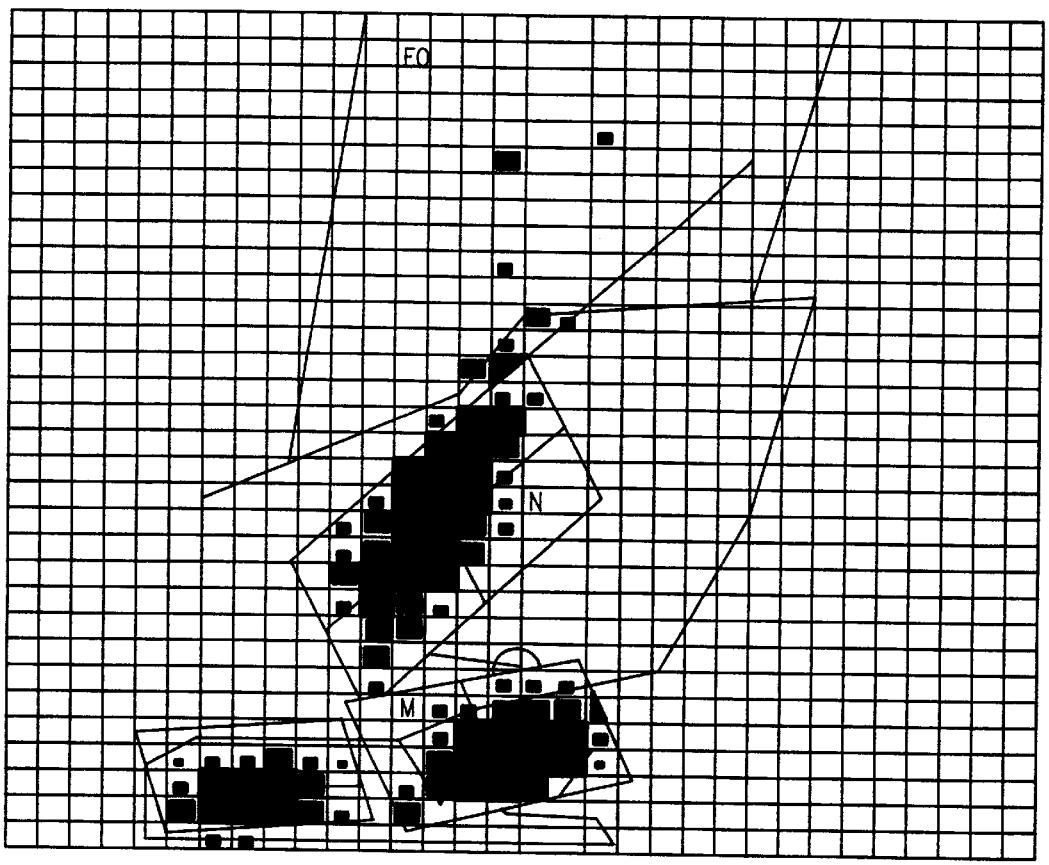
Figure 4:
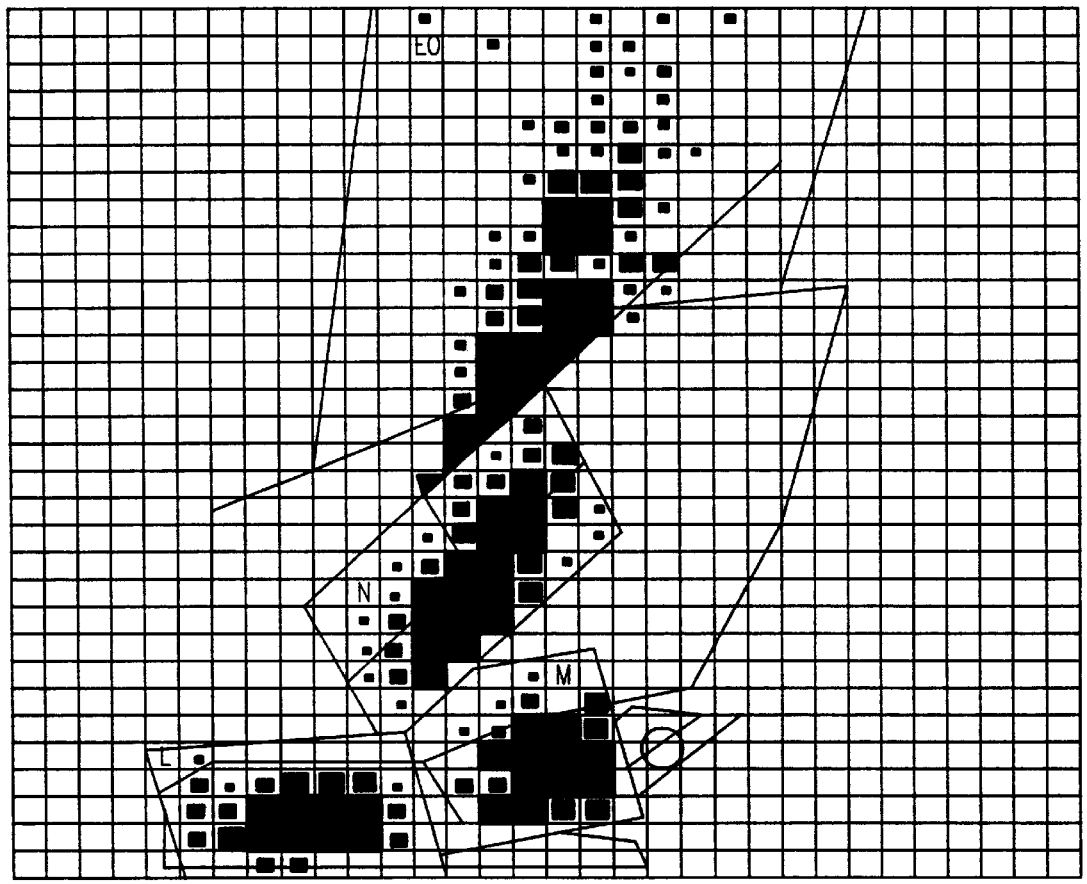

FIG. 2 illustrates, in function of time, three examples of the output voltage evolution of the photodiode amplifier illustrated in FIG. 1.

With reference to FIG. 1, the apparatus according to the invention comprises a tank 1 designed to contain a mixture 2, made up of a blood sample and a determined quantity of lysing agent. These products are introduced by the channel 3 and come from means not represented in FIG. 1.

The tank is closed by a lid 4.

The apparatus comprises means 5 for stirring the mixture and thus ensuring a good homogeneity. These means consists of a rod 6 extending into the tank 1 and fixed in rotation in the lid 4 by means of a bearing 7.

A system ensuring the rotation of the rod 6 in the tank is provided and is not represented in the figure.

At its extremity, the rod 6 includes a part 8 in the form of a blade.

The detection apparatus according to the invention also comprises means 9 of emitting luminous radiation. These means may, for example, consist of an electroluminescent diode. This diode is supplied with electric current by standard means 10.

The means 9 of luminous radiation emission are arranged in such a way that the radiation crosses the tank 1.

The apparatus also contains focusing means 11, such as a focusing lens which is centered on the principal emission axis of the luminous radiation.

Thus, the diode 9 emits luminous radiation in the direction of the lens 11. This radiation constitutes a beam of light directed towards the tank 1 and the mixture 2 which it contains.

The apparatus also comprises means 12 for receiving the light after it has passed in the tank 3; these means of reception may notably consist of a photodiode.

The means of light reception 12 are connected to a system 13 which delivers a signal representative of the quantity of light received by the means 12.

In the case of a photodiode, said photodiode may be connected to an amplifier, delivering an output voltage VO. FIG. 2 illustrates the output voltages obtained, for this embodiment. Depending on its composition, the mixture absorbs to a greater or lesser degree the light emitted by the electro-luminescent diode, and the light received by the photodiode 12 and the output voltage VO of the amplifier 13 also vary in amounts.

The apparatus works as follows. When the mixture 2 is introduced in the tank 1, the lysing agent has not yet affected the blood cells. This mixture generally comprises about 30 μl to which a lysing agent has been added.

The mixture, which is very cloudy, absorbs the luminous radiation emitted by the electro-luminescent diode 9 almost entirely. The voltage from the amplifier 13 is thus approaching 0, as indicated in FIG. 2.

In the course of time, the lysing agent produces its effect and the red blood cells are destroyed. The quantity of light received by the photodiode then increases, along with the output voltage VO of the amplifier 13.

This is illustrated by FIG. 2 which shows three examples of output voltage VO evolution.

In FIG. 2 and as an example, the threshold value of 3 volts is considered as representative of a mixture in which the red blood cells are destroyed, the white blood cells still being intact. This threshold therefore corresponds to the lysis point and to the moment when the lysis must be quenched.

The unbroken straight line (_____) corresponds to an average lysing time, the threshold value of 3 volts being reached after about 8 seconds. The straight line consisting of alternating dashes and circles (-o-o-) corresponds to a shorter lysing time, about 5 seconds, and the straight line consisting of alternating dashes and crosses (-x-x-)to a longer lysing time, of about 19 seconds.

The apparatus according to the invention includes means for detecting that the threshold value is reached. These means are not illustrated in FIG. 1. They may notably consist of a comparator of which a first input is fixed on the previously determined threshold value, a second input receiving the signal emitted by the means 13, representative of the light received by the reception means 12. When the output of the comparator is approximately equal to 0, the mixture present in the tank 1 is ready to undergo analysis, the red blood cells having been destroyed and the white blood cells still being intact. As soon as this value has been detected, the action of the lysing agent must be neutralized. This is notably obtained by dilution with a saline solution at 9 grams per liter of NaCl.

The examples illustrated in FIG. 2 show that the apparatus and process according to the invention make it possible to adapt to the differences existing from one blood sample to another.

The sample corresponding to a mean lysis time of 8 seconds could in fact have been obtained in a valid way according to standard techniques, but this is not the case for the two other examples whose lysing times are respectively 5 and 19 seconds. In point of fact, these standard techniques are based on a fixed lysing time and a mean value, notably 8 seconds. Thus, a blood whose lysing time is 5 seconds would also include destroyed white blood cells if it were prepared according to a standard technique which would continue lysing for 3 extra seconds. Similarly, a blood sample whose lysing time is 19 seconds would include red blood cells if it were prepared according to standard techniques, since lysing would be halted after 8 seconds.

The numerous tests carried out using the process and the apparatus according to the invention have revealed no case in which the blood is incompletely lysed or over-lysed.

Thus, the process and the apparatus according to the invention make it possible to overcome the drawbacks of known techniques by no longer using a fixed lysing time but by adapting it to each type of blood prepared. In this way, said process and apparatus make it possible to take into account the differences existing from one blood sample to another, these differences depending notably on the age of the sample, that is to say on the moment when it was collected from the patient. So-called autolysis phenomena have in fact been observed when the sample has been stored for too long.

What is claimed is:

1. A method for isolating and differentiating leucocytes in a blood sample comprising the following steps:

lysis of the erythrocytes with a solution whose osmolality and pH have been adjusted to maintain leucocyte integrity, and containing saponin, determination of the point of lysis at that point, and inhibition of the lysis by diluting the sample with a solution having a substantially similar composition but not containing saponin.

2. A method according to claim 1, which comprises determining the point of lysis by measuring the light radiation emitted through the sample.

3. A method according to claim 1, which comprises quantifying and differentiation isolated leucocytes by flow cytometry.

4. A method according to claim 1, which comprises diluting the reaction medium derived from the lysis step with the solution not containing saponin in a ratio of between 2 and 4.

5. A method according to claim 1, wherein the lysis temperature is between 15° and 45° C.

6. A method according to claim 1, which comprises carrying out the lysis of erythrocytes using an erythrocyte lysis reagent in the blood sample, the reagent comprising 0.1 to 2 g/l of saponin and having an osmolality between 200 and 400 milliosmoles and a pH between 6 and 8.

7. A method according to claim 1, wherein the lysis temperature is about 37° C.

* * * * *